United States Patent
Tveras

[11] Patent Number: 5,810,856
[45] Date of Patent: Sep. 22, 1998

[54] WIPING ELEMENT FOR AN ORAL HYGIENE DEVICE, WINDOW WIPER, OR THE LIKE

[76] Inventor: Rimvydas Tveras, 8945 W. 103rd St., Palos Hills, Ill. 60465

[21] Appl. No.: 705,271

[22] Filed: Aug. 29, 1996

Related U.S. Application Data

[63] Continuation-in-part of Ser. No. 401,421, Mar. 9, 1995, abandoned.

[51] Int. Cl.$^6$ .................................................. A61B 17/24
[52] U.S. Cl. ............................................. 606/161; 15/111
[58] Field of Search ........................... 606/161; 15/111, 15/236.01, 187, 188, 245

[56] References Cited

U.S. PATENT DOCUMENTS

| | | |
|---|---|---|
| 1,891,864 | 12/1932 | Barrett . |
| 1,910,414 | 5/1933 | Varga ......................................... 15/245 |
| 2,167,196 | 7/1939 | Bothum . |
| 2,574,654 | 11/1951 | Moore . |
| 3,254,356 | 6/1966 | Yao et al. . |
| 3,359,588 | 12/1967 | Kobler . |
| 4,455,704 | 6/1984 | Williams . |
| 4,610,043 | 9/1986 | Vezjak . |
| 5,005,246 | 4/1991 | Yen-Hui . |
| 5,032,082 | 7/1991 | Herrer . |
| 5,211,494 | 5/1993 | Baijnath . |
| 5,226,197 | 7/1993 | Nack et al. . |
| 5,528,793 | 6/1996 | Schbot ....................................... 15/245 |
| 5,546,625 | 8/1996 | Mealey, Sr. ............................... 15/105 |

*Primary Examiner*—Michael Powell Buiz
*Assistant Examiner*—Daphna Shai
*Attorney, Agent, or Firm*—Leydig, Voit & Mayer, Ltd.

[57] ABSTRACT

A wiping or scraping device, particularly for cleaning a human tongue, is provided having one or more wiping teeth or wiping elements. Each tooth or element has at least one scoop-like side which terminates at a wiping edge or ridge in an undercutting fashion. Various embodiments are provided for providing bi-directional or planar-directional wiping or cleaning action. For example, embodiments of the invention include wiping devices, linear wiping elements or circular wiping elements with outwardly-directed and/or inwardly-directed annular wiping edges. The wiping device may include a plurality of wiping elements arranged in a row or array. Embodiments are provided wherein the wiping device is configured for use as a windshield wiper or squeegee.

21 Claims, 7 Drawing Sheets

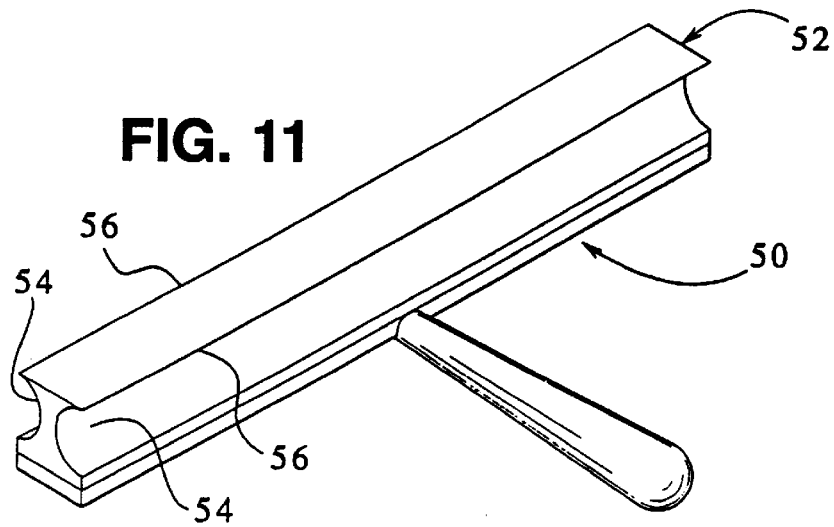
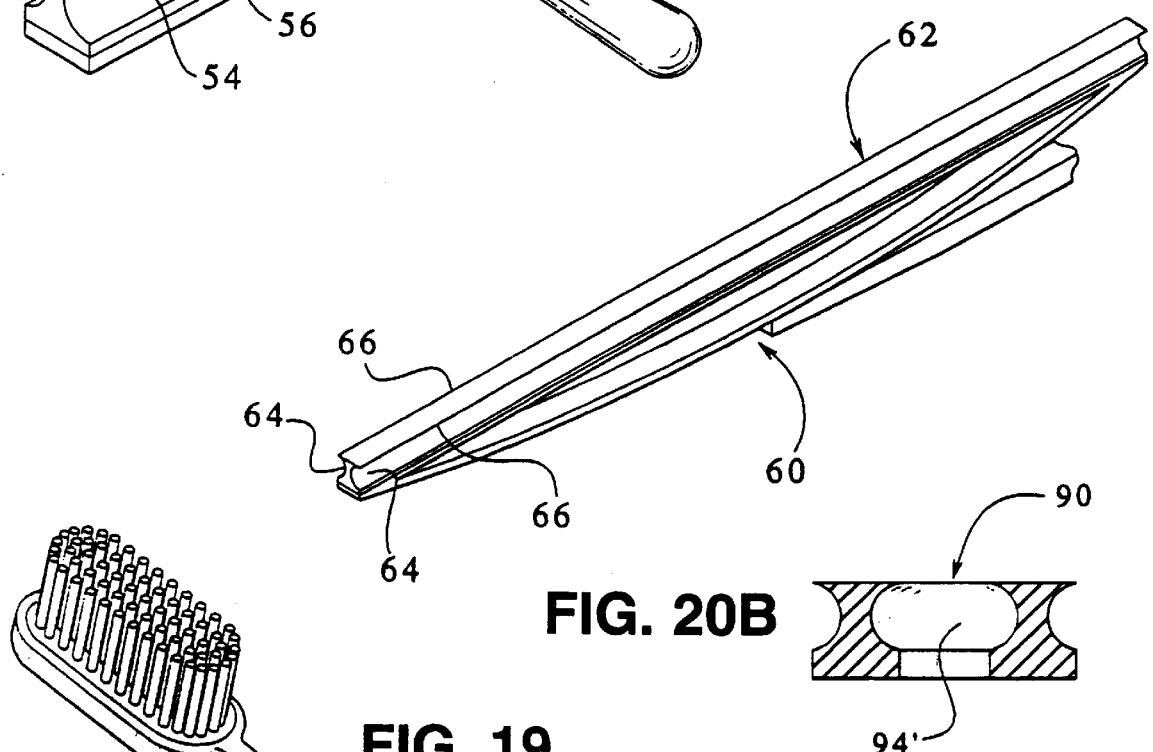
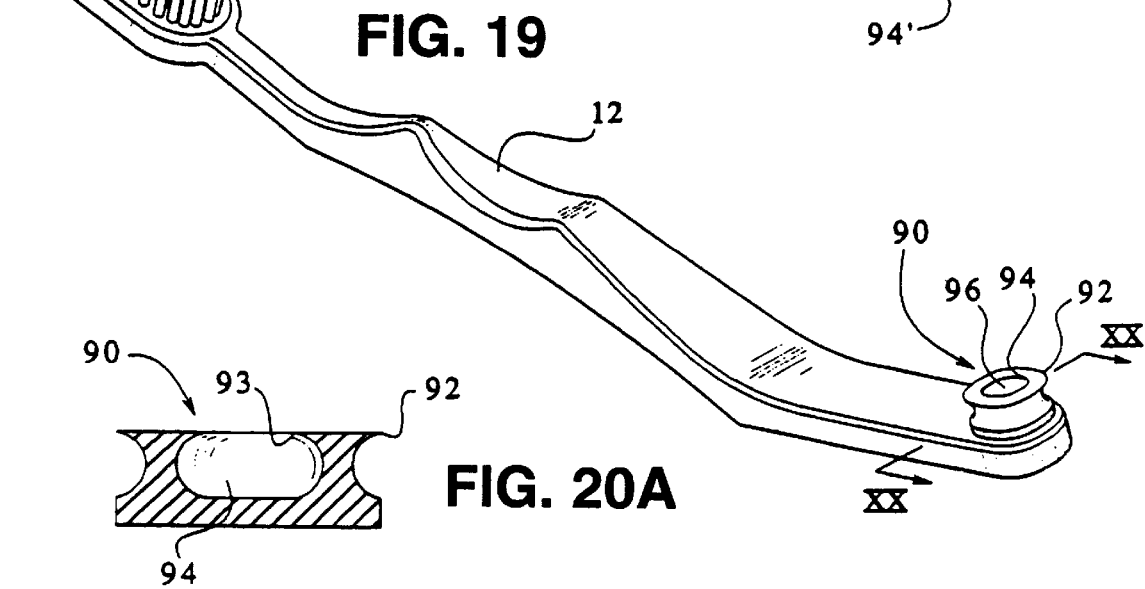

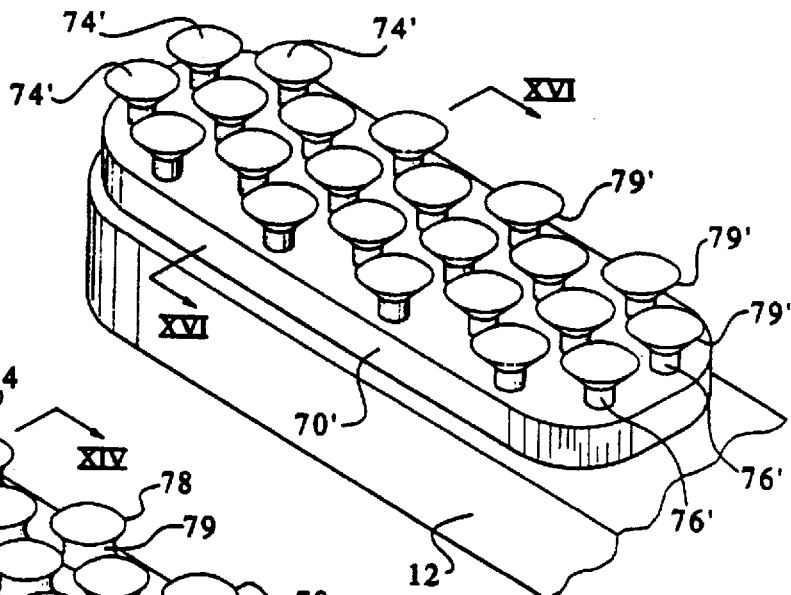
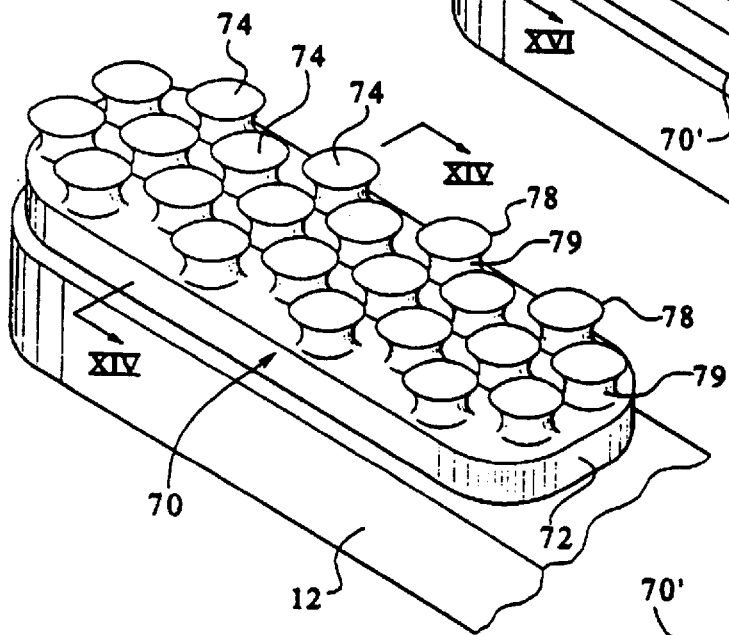
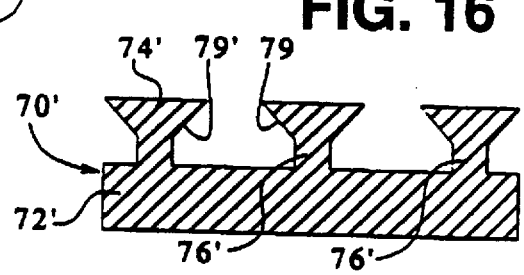
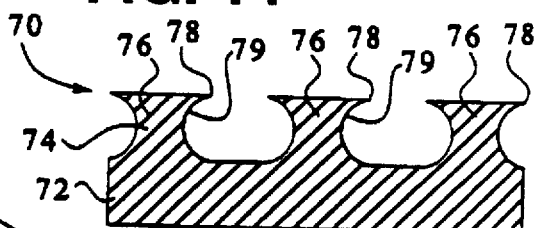
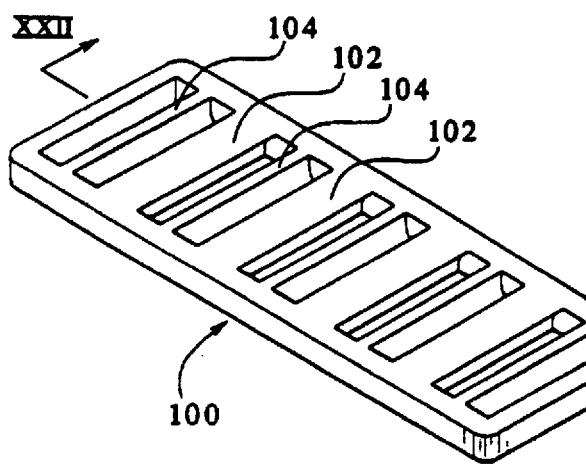
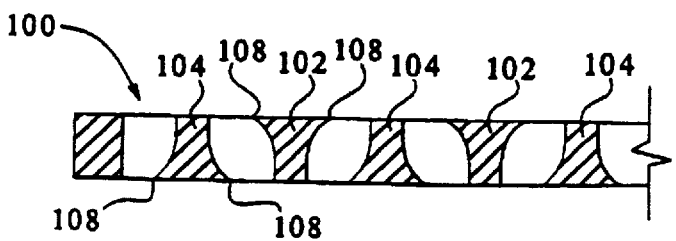

WIPING ELEMENT FOR AN ORAL HYGIENE DEVICE, WINDOW WIPER, OR THE LIKE

CROSS REFERENCE TO RELATED APPLICATION

This is a continuation-in-part of U.S. patent application Ser. No. 08/401,421, filed Mar. 9, 1995 now abandoned.

BACKGROUND OF THE INVENTION

FIELD OF THE INVENTION

The present invention generally relates to a flexible wiping or scraping element suitable for wiping, scraping and cleaning undesirable accumulations of material from a surface. In various embodiments, the element is useful as a human tongue cleaner, a squeegee, a wiper blade, or the like.

It is recognized that regular tongue cleaning is an important part of maintaining good oral hygiene. The surface of a human tongue is irregular in shape, having papillae, taste buds, nodules, furrows, folds, grooves and fissures. These irregularities provide spaces which can trap film and materials such as food particles, plaque, mucus, sinus drainage, etc. When a tongue remains uncleaned for a period of time, such debris can permit bacterial growth, and cause problems such as bad breath. Therefore, regular tongue cleaning is beneficial.

Although tongue-cleaning is widely recognized as being advantageous, specific tongue-cleaning devices have heretofore not been widely used. Rather, a conventional means of tongue cleaning is by brushing with a toothbrush. Unfortunately, tongue-brushing with a toothbrush is not optimally effective and can result in premature toothbrush bristle wear. However, the time at which one brushes his teeth is a convenient tongue-cleaning time.

An example of a known tongue cleaner is shown in U.S. Pat. No. 1,891,864 which relates to a tongue cleaner brush having an adjacent scraping plate. One embodiment includes a plurality of straight, cylindrical rubber fingers. Also, U.S. Pat. Nos. 2,574,654; 3,254,356; 4,455,704 and 5,005,246 relate to a blade or plate-type tongue scraper in combination with a toothbrush.

A single-edged blade type cleaning or wiping element, such as a conventional windshield wiper or squeegee blade, or a straight finger-shaped element such as a brush bristle, initially contacts a surface at a generally right angle. If the element is flexible, the element bends and tends to lie down against the surface as the element drags as the element is dragged across, engaging the surface at less than a right angle. For example, a windshield wiper flexes and partly lies down against a windshield in such a manner.

Unfortunately, this flexing behavior of a conventional blade or bristle results in pushing materials downward into the surface. A lifting or hydroplaning effect can thereby occur, wherein fluid is pressurized by the wiping or scraping element, lifting the flexed element from the surface. In an irregular surface, such as a tongue, the pressing-in effect of a conventional blade or bristle is particularly undesirable as the unwanted debris may be spread along and forced into recesses.

Therefore, an object of the invention is to provide an improved wiping or scraping element which lifts, scoops and removes debris from a surface, and which eliminates the pressing-in of debris and fluid against the surface. Moreover, another object is to provide such an element which operates bi-directionally in the same manner, for use in a back-and-forth wiping motion.

SUMMARY OF THE INVENTION

An embodiment of the present invention achieves the aforementioned objects by providing an improved oral hygiene device which effectively removes debris from a tongue's irregular surface. The oral hygiene device or tongue cleaner of the present invention can further be conveniently integrated into a toothbrush handle. Such a device is inexpensive to manufacture and is aesthetically pleasing.

To this end, in an embodiment, the present invention provides an oral hygiene device, or tongue cleaner, which has wiping device including a one or more flexible elements. In a preferred embodiment, each of the wiping elements has at least one curved side forming an undercut wiping edge or ridge which meets the surface at greater than a 90° angle, so that debris is lifted away rather than being pressed in.

In the wiping device of the present invention, the wiping member is operable when moved in at least one direction—a direction perpendicularly toward the curved side. The present invention provides an improved oral hygiene device which effectively removes debris from a tongue's irregular surface. The oral hygiene device or tongue cleaner of the present invention can further be conveniently integrated into a toothbrush handle. Such a device is inexpensive to manufacture and is aesthetically pleasing. To this end, in an embodiment, the present invention provides an oral hygiene device, or tongue cleaner, which has a plurality of curved teeth. In a related embodiment, each of the teeth is wave-shaped having a concave side and an opposite ramped side. The two sides meet in a crest or ridge. The ridge can be formed by a row of rounded extremities. In an embodiment of the present invention, the tongue-cleaning teeth can be incorporated into a toothbrush handle. In such an embodiment, the oral hygiene device includes an elongated handle to which the teeth are secured near one end. A toothbrush head is disposed at an opposite end of the handle.

An embodiment of the present invention provides a tongue cleaner which bi-directionally operates in a push-pull manner. In such an embodiment, a plurality of rows of slanted teeth are provided. At least one of the rows is slanted in one direction while at least one other row is slanted in the opposite direction, so that at least one of the rows is moving against the direction of its slant. Also, in an embodiment, alternate adjacent rows can be oppositely tapered in width. Such an opposite tapering results in highly effective tongue cleaning, with narrower teeth fitting into smaller recesses of a tongue surface.

In an embodiment, the wiping device is configured for optimal bi-directional use, cleaning along an entire width of the device while alternately operating in either of two opposite wiping directions along a wiping axis. This is achieved either by providing each wiping member with oppositely-directed curved sides.

Specifically, to this end, a wiping device is provided with a base and at least one resilient wiping element. This wiping element includes a pedestal wall projecting generally perpendicularly from the base. The pedestal wall has a first end connected to the base and a second free end spaced from the base. The pedestal wall has two curved or angled and oppositely-facing parallel longitudinal sides extending between the base and the free end, wherein the pedestal wall has a varying thickness between the sides which increases in a direction toward the free end. A pair of parallel wiping edges are adapted for engaging and abrading the surface. Each of the wiping edges are formed at an undercutting termination of a respective one of the curved sides at the free end.

In a preferred tongue-cleaning embodiment of the double-acting device, multiple wiping elements are arranged parallel to each other.

In an embodiment, the longitudinal sides of the pedestal wall are shaped as a partial cylinders. Where multiple elements are provided, the respectively facing undercut sides of adjacent wiping elements can be respectively formed by a plurality of generally cylindrical bores extending transversely through the base.

Also, in an embodiment, a double-acting wiping element can be provided with a plurality of slots extending from the free end at least partially to the base, the slots being aligned generally along the axial wiping direction. This feature permits segments of the slotted wiping element to flex independently, improving the cleaning action on irregular surfaces.

The double-acting device can also be configured for use as a squeegee or windshield wiper. Such a squeegee or wiper can have a single wiping element, but a multiple-element embodiment is within the realm of the invention.

In another embodiment, the device is configured for operation in any direction within a wiping plane. This is achieved by providing the device with a circular wiping member having an annular curved wall. The annular wall results in a scooping or lifting action when moved over a surface in any direction. In another planar-directional embodiment, the device is provided with one or more shaped apertures formed by annular curved walls. Both of these embodiments include an circular wiping edge which is undercut by a shaped annular side to provide the desired "lifting" or "scooping" wiping action, as opposed to a "pressing-in" effect.

Specifically, such a planar-directional wiping device includes a base and at least one circular wiping element. The wiping element has a circular pedestal wall projecting generally perpendicularly from the base, the pedestal wall having a first end connected to the base and a second free end spaced from the base. The pedestal wall has an annular side extending between the base and the free end, wherein the annular side has a varying circumference which increases in a direction toward the free end. An annular wiping edge is formed at a termination of a the annular side at said free end. The annular wiping edge is adapted for engaging and abrading a surface, such as a tongue, when moved in any direction within a plane of the annular wiping edge.

Preferably, a plurality of circular wiping elements are arranged in an array on the base. In an embodiment, the wiping element has a cylindrical recess opening to the free end so that the pedestal is at least partially hollow.

Especially for a tongue cleaner embodiment, the wiping element preferably has multiple wiping members arranged parallel to each other for simultaneous action of multiple members against the surface.

In an alternative construction, the annular wiping edge can be embodied in a wiping device having a plate-like base with a wiping side, wherein at least one shaped aperture extends through the base. The annular wiping edge is formed where the aperture opens to the wiping side. The aperture has an oblate spheroidal cross-section as viewed perpendicularly to the wiping side so that the aperture undercuts the wiping side at the wiping edge.

Preferably, a plurality of the shaped apertures are arranged in an array in the base.

Preferably, the wiping devices are made of a resilient material such as rubber or plastic. Being resilient, the wiping elements are more comfortable and can deflect to more closely follow a tongue's irregular contour to scoop off scale and debris. Therefore, an advantage of the present invention is to provide a tongue cleaner which is highly effective at removing undesirable material from a tongue's irregular surface.

An advantage of the present invention is to provide a tongue cleaner which is highly effective at removing undesirable material from a tongue's irregular surface.

Another advantage of the present invention is to provide a bi-directional double-acting wiping or scraping device which operates equally well when moved in either of two opposite wiping or scraping directions.

Yet another advantage of the present invention is to provide a tongue cleaner which is simple and inexpensive to manufacture.

Embodiments of the present invention can be attractively formed, particularly in multi-tooth or multi-element embodiments. Thus, the invention provides a further advantage of providing a tongue cleaner which is aesthetically pleasing.

An additional advantage of the present invention is to provide a tongue cleaner which can be conveniently and comfortably disposed in a toothbrush handle.

Another aspect of the present invention is that use of the tongue cleaner can reduce one's chances of catching colds and disease. Cleaning one's tongue with the device of the invention is an effective means of removing germs and bacteria from the mouth, some of which may cause colds or other illnesses. Accordingly, the tongue cleaner of the present invention is believed to advantageously reduce a user's chances of catching colds and illness.

Additional features and advantages of the present invention are described in and will be apparent from, the detailed description of the presently preferred embodiments and from the drawings.

BRIEF DESCRIPTION OF THE DRAWINGS

FIG. 11 is a perspective view of a squeegee incorporating the double-acting wiping element of the present invention.

FIG. 12 is a perspective view of a windshield wiper incorporating the double-acting wiping element of the present invention.

FIG. 13 is a fragmentary perspective view of a planar-directional wiping device having an array of circular wiping elements having curved annular sides, the device being mounted on a toothbrush handle.

FIG. 14 is a cross-sectional view taken generally along line XIV—XIV of FIG. 13.

FIG. 15 is a fragmentary perspective view of a planar-directional wiping device having an array of circular wiping elements having angularly annular sides, the device being mounted on a toothbrush handle.

FIG. 16 is a cross-sectional view taken generally along line XVI—XVI of FIG. 15.

FIG. 19 is a perspective view of a ring-shaped wiper device in an embodiment mounted on a toothbrush handle.

FIG. 20A is a sectional view taken generally along line XX—XX of FIG. 19, in an embodiment having a closed bottom.

FIG. 20B is a sectional view of an alternative ring-shaped wiper embodiments having an open bottom.

FIG. 21 is a perspective view of a wiping device having a plurality of elongated one-sided wiping elements.

FIG. 22 is a cross-sectional view taken generally along line XXII—XXII of FIG. 21.

DETAILED DESCRIPTION OF THE PRESENTLY PREFERRED EMBODIMENTS

Figure 1:
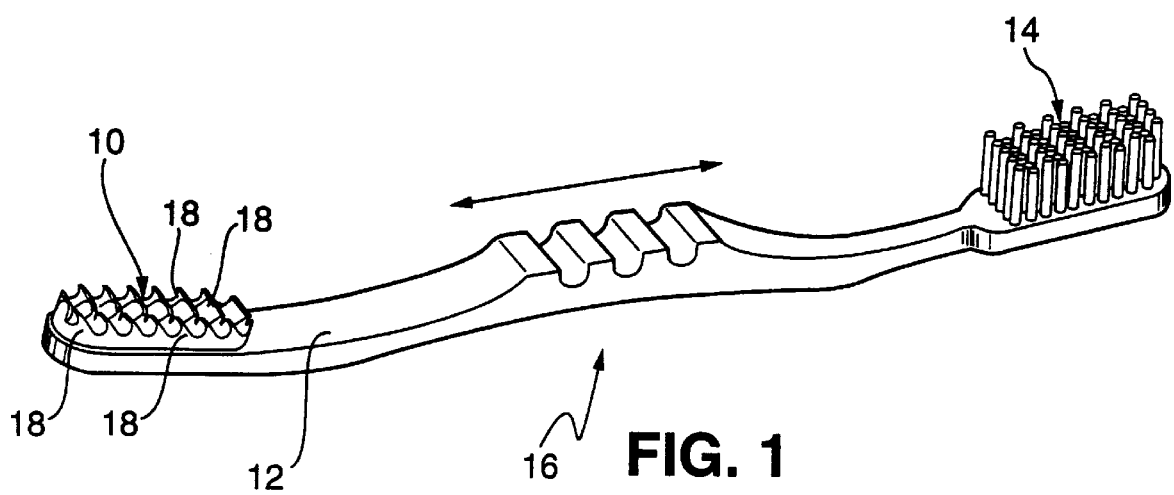
FIG. 1 illustrates a perspective view of an embodiment of the oral hygiene device according to the present invention including the tongue-cleaner element which is integral to a toothbrush handle.

The present invention provides a tongue cleaner device 10 which can be a single, molded piece. As illustrated in FIG. 1, the tongue cleaner device 10 can be secured in an integral fashion with a toothbrush. As shown, the tongue cleaner device 10 is recessed and secured in an elongated toothbrush handle 12, having a toothbrush head 14 disposed at an opposite end. The resulting combination is a convenient oral hygiene tool 16 which can be simply flipped over for using either the toothbrush head 14 or the tongue cleaner device 10. The tongue cleaner device 10 can be used either before or after brushing, and with or without toothpaste.

Figure 2:
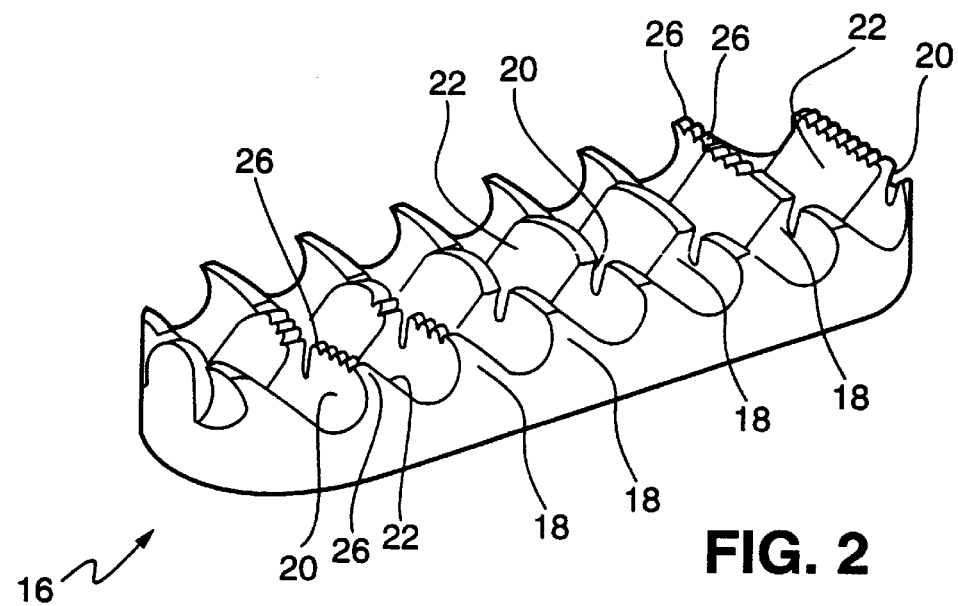
FIG. 2 illustrates an isolated perspective view of the embodiment of the tongue-cleaner element of FIG. 1.

FIG. 2 illustrates the tongue cleaner device 10 in greater detail. The tongue cleaner device 10 includes a plurality of resilient teeth 18. The teeth 18 can be arranged in a plurality of rows, e.g., three rows, as illustrated in FIG. 2. In an embodiment, each tooth 18 is slanted or curved toward a direction of operational motion. In the embodiment illustrated, each tooth 18 is slanted or curved in the general direction of operation of the toothbrush, as indicated by the arrows in FIG. 1. Correspondingly, each tooth 18 has a concave curved side 20 inclined more than 90° from the horizontal and an opposite ramped side 22. This gives each tooth 18 a wave-like shape, forming a concave scoop or cup at the curved side 20. The curved side 20 and ramped side 22 meet in a respective ridge which can be pulled along a tongue's surface removing debris. This debris then collects in the concave space of the curved side 20 to be removed from the mouth. The debris can simply be rinsed off with water after use, leaving the tongue cleaner device 10 clean.

Figure 3:
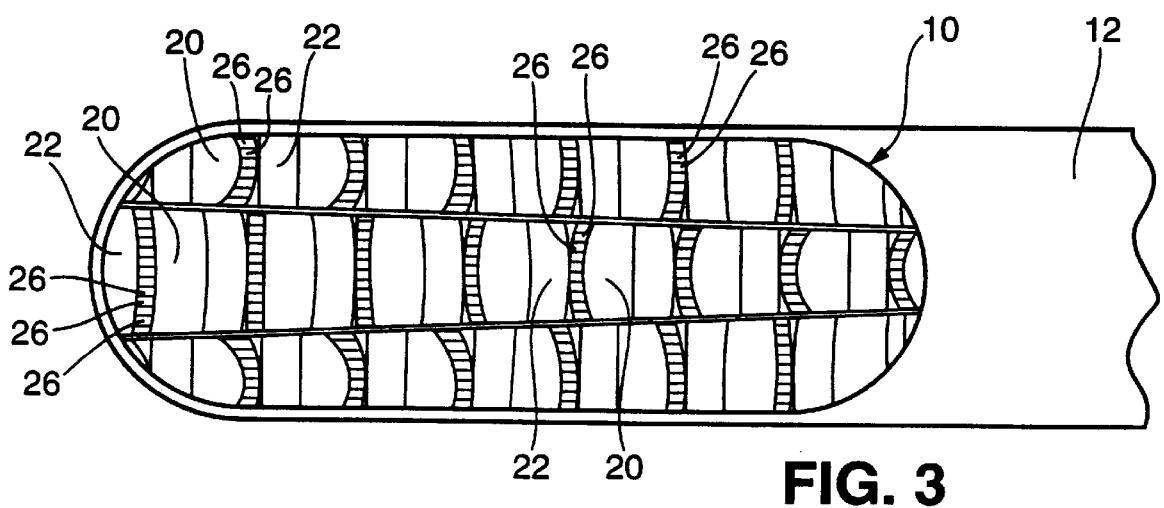
FIG. 3 illustrates a partial top plan view of the oral hygiene device of FIG. 2.
Figure 4:
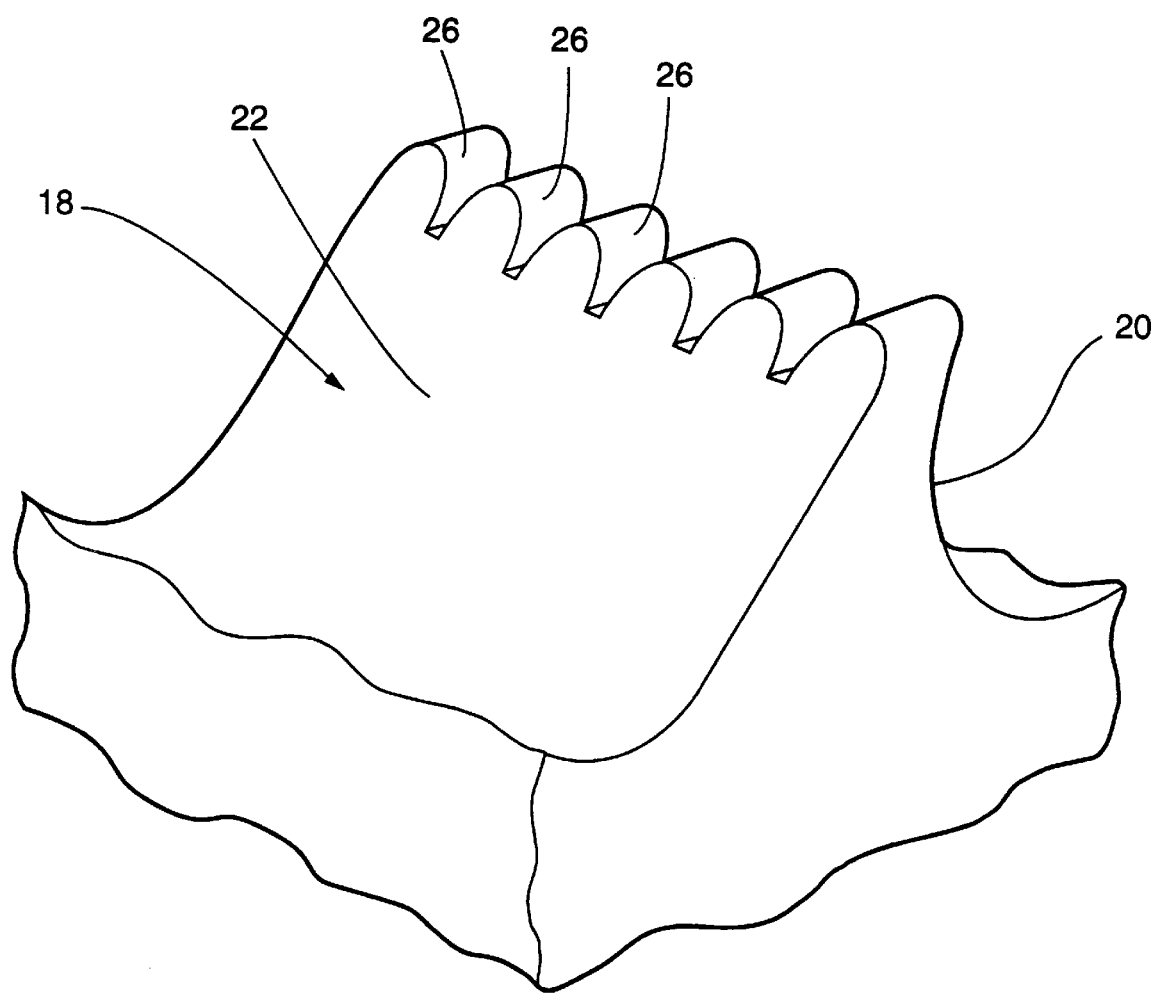
FIG. 4 illustrates a partial perspective view of one of the teeth.

As illustrated in FIGS. 2, 3, and especially the enlarged view of FIG. 4, the ridge of each tooth 18 preferably has a plurality of extremities 26. Each extremity 26 is small and rounded in shape to fit into small spaces on a tongue surface. Note that FIG. 2 illustrates only some of the extremities 26 for clarity.

In an embodiment wherein the tongue cleaner device 10 has multiple rows, as illustrated in FIGS. 1–3, adjacent rows are preferably oppositely directed. As shown, the middle row of teeth 18 faces in one direction and the outer rows of teeth face oppositely. Thus, the tongue cleaner device 10 provides a push-pull cleaning action against a tongue as a user moves the tongue cleaner device 10 back and forth in a bi-directional motion, as indicated by the arrows in FIG. 1.

The tongue cleaner device 10 is preferably made of a resilient, molded plastic so that each tooth 18 is flexible. This allows the teeth 18 to deflect and conform to tongue surface irregularities. As the tongue cleaner device 10 is moved over a tongue surface, at least one of the rows has its respective curved sides 20 moving forward. As the ridge of each of these respective teeth 18 frictionally contacts the tongue surface, the corresponding curved side 20 reacts and stretchably elongates with a cupping action, pressing against the tongue. The adjacent row or rows of teeth 18 tend to resiliently lie down, increasing the cleaning effect of the forward-moving rows.

As illustrated in FIG. 3, each row of teeth 18 can be tapered in width. Preferably, adjacent rows are oppositely tapered, one row widening as the adjacent row narrows. The opposite tapering results in a cooperative fit between the rows. Furthermore, opposite tapering results in greater cleaning effectiveness as the tongue cleaner device 10 is dragged over the surface of the tongue. Coincidentally, the tapered, oppositely directed pattern of teeth 18 gives the tongue cleaner device 10 an attractive and unthreatening appearance—an advantage over some prior art scraping-plate type tongue cleaners.

As mentioned, the present invention also provides a double-acting wiping configuration for optimal bi-directional operation. An example of such a wiping device 30 is illustrated in FIGS. 5–10, in the embodiment of a tongue cleaner. The double-acting wiping device 30 can also be a single, molded piece.

Figure 5:
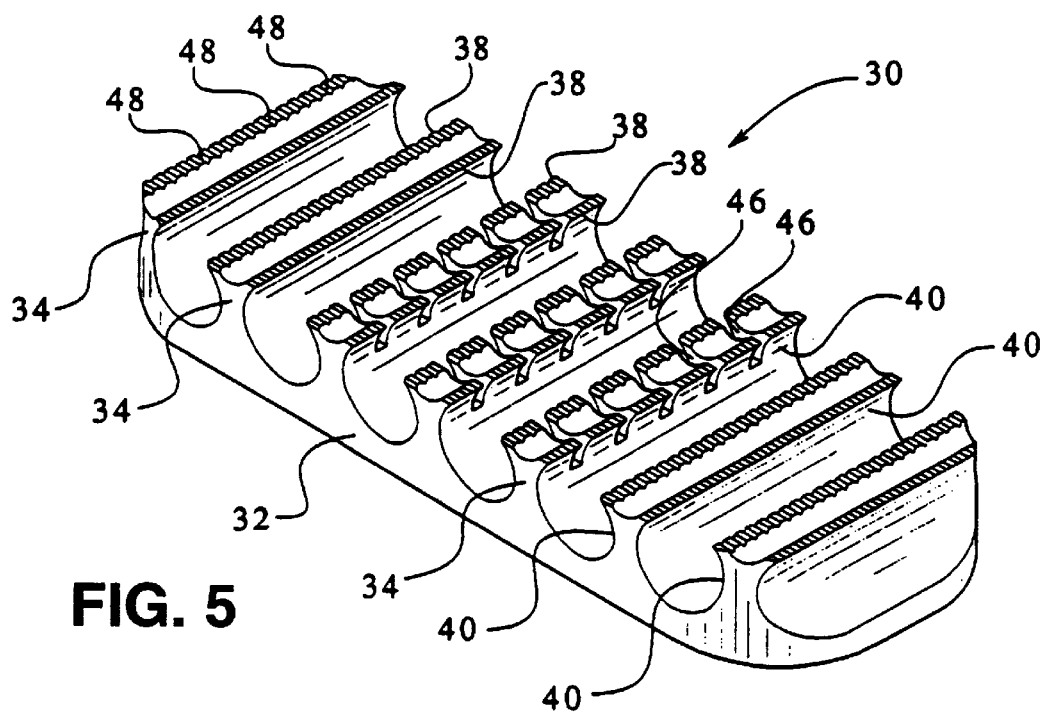
FIG. 5 is a perspective view of an embodiment of the invention configured or use as an oral hygiene device according to a double-acting embodiment of the resent invention.
Figure 7:
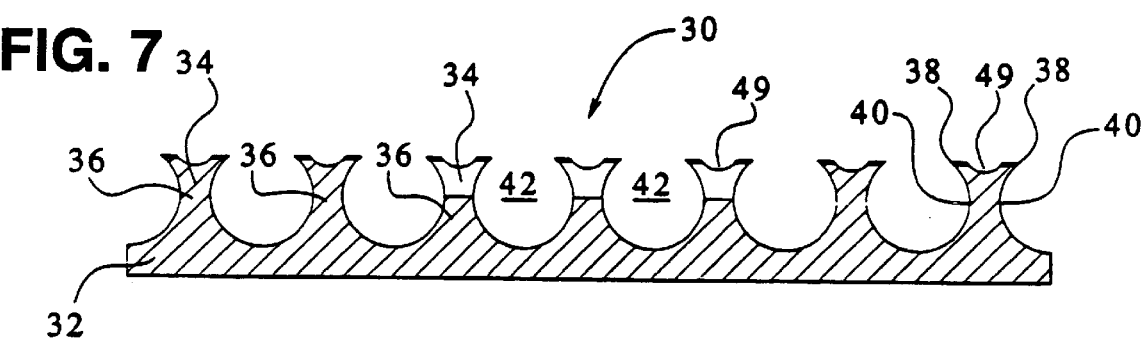
FIG. 7 is a sectional side view taken generally through line VII—VII of FIG. 6.

Referring to FIGS. 5 and 7, the tongue cleaner device 30 includes a base 32 which is generally flat or plate-like in shape. A plurality of teeth or wiping elements 34 extend from the base, each of which has central pedestal wall 36 having a first end connected to the base. Also each central pedestal wall 36 has a second free end with a pair of oppositely-directed, parallel wiping edges 38 formed by opposite scoop-like sides 40 which may be curved or angled sides. These wiping edges 38 form crested, elongated linear ridges, but as will be apparent below, embodiments of the invention are possible having wiping elements with non-linear or circular wiping edges.

As illustrated in FIG. 7, these sides 40 are respectively shaped in an undercutting and sloping fashion, terminating at the free end of the wiping element 34 to form oblique angles at the wiping edges 38. In a preferred embodiment of the tongue cleaner device 30, the opposing curved sides 40 of adjacent wiping elements 34 are formed by cylindrical bores 42, as illustrated by FIG. 7.

In other terms, the pedestal wall 36 has a varying thickness (dimension in the axial direction) which is at a minimum at a middle region, the thickness increasing in a direction toward the free end. A maximum width of the pedestal wall 36 is present at the wiping edges 38. This gives the wiper elements 34 a crest-like undercut angled or curved shape under each wiping edge 38. The free ends, and wiping edges 38 thereon, form a flat top which generally lies in a wiping plane.

Figure 8:
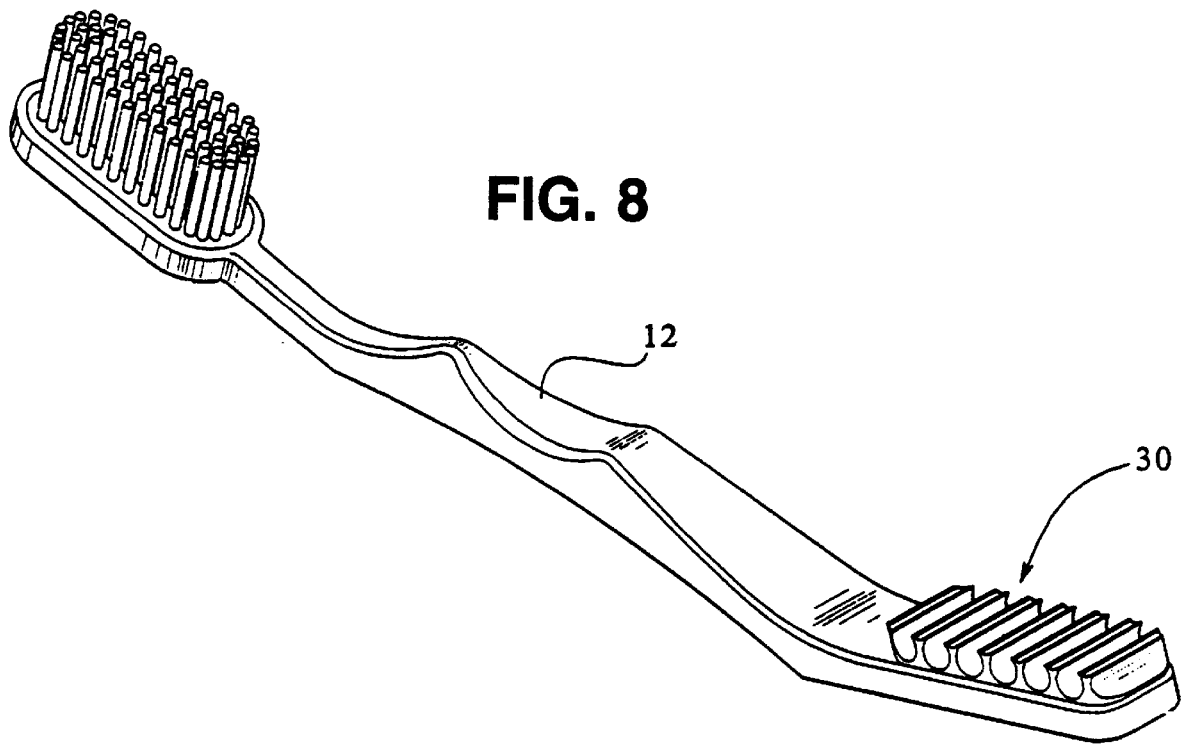
FIG. 8 is a perspective view of the device of FIG. 1 in combination with a toothbrush wherein the device is mounted on a toothbrush handle.
Figure 6:
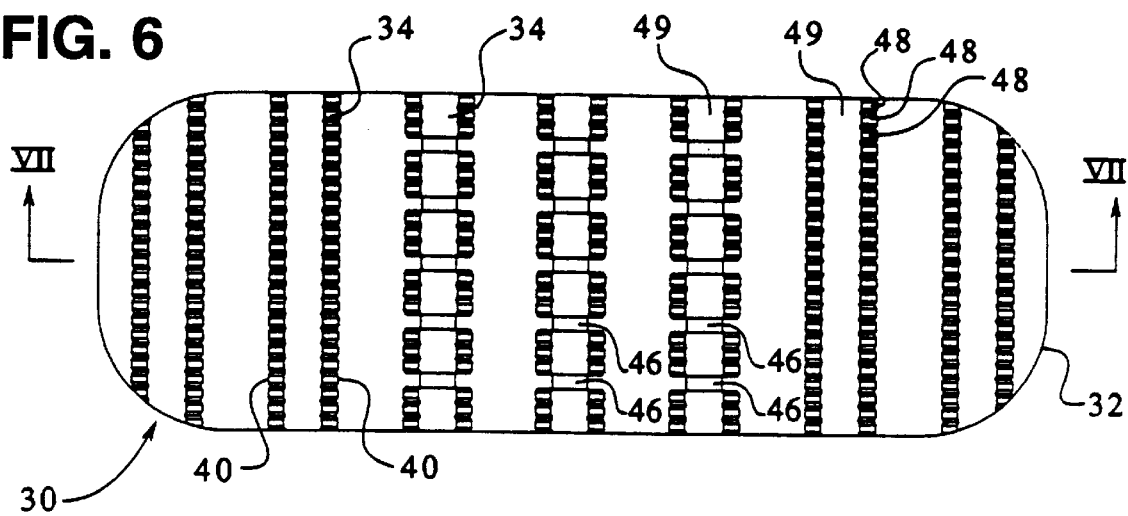
FIG. 6 is a plan view of the device of FIG. 5.

As shown in FIGS. 5 and 6, the plurality of wiping elements 34 are arranged in a parallel fashion, having opposing scoop-like curved sides 40. As illustrated in FIG. 8, the tongue cleaner device 30 is securable in an integral fashion with a toothbrush handle 12 for convenient tongue cleaning. Because of the parallel arrangement of the wiping elements 34, the device 30 be pulled along a tongue's surface, removing debris equally well in either of two directions.

As mentioned, the tongue cleaner device 30, and all embodiments herein, are preferably made of a resilient, molded plastic so that wiping elements 34 are flexible. This allows the teeth 18 to deflect and conform to tongue surface irregularities.

Figure 9:
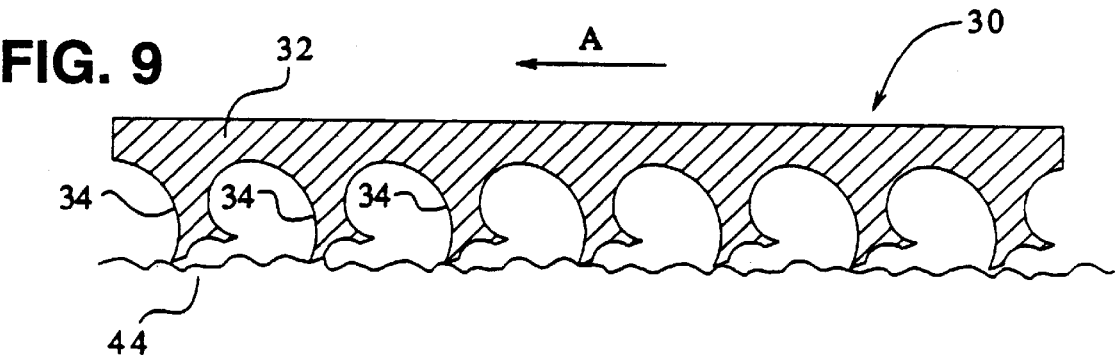
FIGS. 9 and 10 are sectional side views of the device of FIG. 5 in operational wiping motion along respectively illustrated alternating directions.
Figure 10:
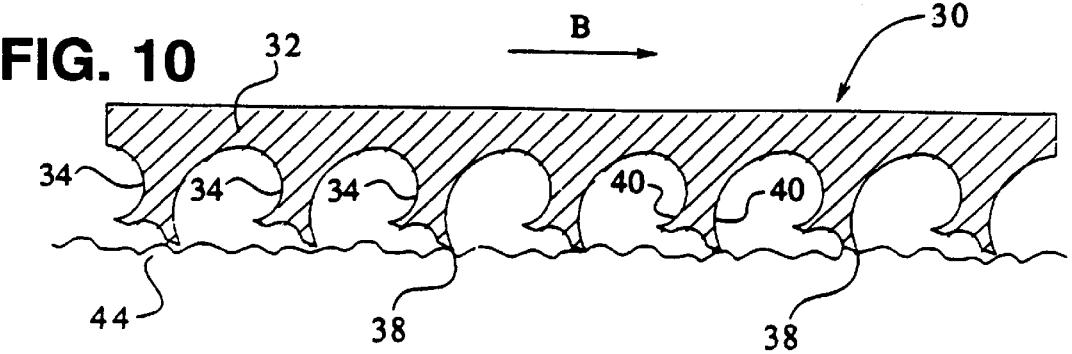

More specifically, as illustrated in FIGS. 9 and 10, the wiping element 30 can be moved in a reciprocating axial manner in directions A (FIG. 9) and B (FIG. 10). In a preferred embodiment, wherein the device 30 is resilient, the wiping elements 34 flex in a common direction to engage the respective leading wiping edges 38 against a tongue surface 44. Debris then collects in the concave bore between the curved sides 40 to be removed from the mouth. The debris can simply be rinsed off with water after use, leaving the tongue cleaner device 40 clean.

In the resilient embodiment, each member is advantageously designed in terms of dimensions and stiffness such that the leading wiping edge drags over the surface so that the scoop-like side meets the tongue at an of less than 90° relative to the tongue, in the manner shown in FIGS. 9 and 10. This results in a "lifting" of debris away from the tongue, in contrast to the "pressing-in" effect caused by conventional blade-type wipers.

Also, as the leading wiping edge 38 of each of these respective wiping elements 34 frictionally contact and abrade against the tongue surface 44, the corresponding curved side 40 reacts and stretchably elongates with a cupping action against the tongue. A bias force of the wiping elements 34 to stand up causes an increased cleaning effect of the forward-moving wiping edges 38.

Another advantage of the flexible wiping elements 34 is that the trailing wiping edges lift upwardly, preventing the spread of removed debris (which has accumulated on the undercut side 40) back onto the tongue when the direction is reversed.

The resilient aspect may be further enhanced by providing one or more slots 46 in selected wiping elements 34, as indicated in FIGS. 5 and 6. These slots 46 separate the respective wiping element into segments which are independently flexible, improving the cleaning action of that wiping element over an irregular, non-smooth surface.

A optional feature for enhancing performance of the wiping edges 38 includes a plurality of grooves 48, indicated in FIGS. 5 and 6, which are arranged at the wiping edges 38 and aligned in the direction of bi-axial operational motion. Like the rounded extremities of the embodiments described in connection with FIGS. 1–4, the grooves 48 allow the wiping edges 38 to reach into small recesses in a tongue surface.

Moreover, a longitudinal channel 49, indicated in FIGS. 6 and 7, can optionally be disposed within the free end of each wiping element 34. The channel 49 extends along a width of the wiping element and centrally separates the parallel wiping edges 38. Depending on the stiffness and dimensions of the material used to construct the wiping device 30, the channel 49 may improve the performance of the wiping edges 38 by increasing the degree of flexibility at that region.

The double-acting aspect of the present invention configuration can also be utilized in other areas. For example, FIG. 11 illustrates a squeegee 50 having a single wiper element 52 of similar construction to that described in connection with FIGS. 5–10 above. Also, FIG. 12 illustrates a windshield wiper 60 having a single wiper element 62.

The wiper elements 52, 62 also include scoop-like parallel sides 54, 64, respectively, which form oppositely-directed wiping edges 56, 66, respectively. Of course, such wiping elements 52, 62 lift material from glass or another surface when moved across the surface in either of two transverse directions. Embodiments of the squeegee 50 or windshield wiper 60 could be provided which have multiple wiper elements.

The windshield wiper 60 may be configured for advantageous operation on vehicles having high airspeeds. For example, on airplanes or automobiles, a conventional windshield wiper can lift and hydroplane on the glass. This is at least partially due to the wedge-shaped pocket forming between a conventional wiper blade and the glass receives air pressure at high vehicle speeds which forces the wiper blade away from the glass. In the present invention, the undercut shape of the wiping element can act under air pressure to force the wiper 60 against the glass, thereby improving the wiping effect and eliminating hydroplaning.

Now turning to FIG. 13, the present invention also provides a wiping device 70 which is planar-directional in operation, or rather, is not limited to wiping only bi-axially. The wiping device 70 also has a generally plate-like base 72. A plurality of circular wiping elements 74 extend from the base in an array. As shown in FIG. 14, each of the circular wiping elements 74 has central circular pedestal wall 76 with a first end connected to the base. Also each circular pedestal wall 76 has a second free end with an annular wiping edge 78. These free ends form generally flat tops on the wiping elements 74 which lie in a wiping plane.

The annular pedestal wall 76 is flared in shape, having a circumference which is smallest in a middle section of the pedestal wall, increasing in a direction toward the free end, maximizing at the annular wiping edge 78. This defines a scoop-like annular side 79 having an undercutting shape for achieving the cupping cleaning action like the above described embodiments with linear wiping edges.

FIGS. 15 and 16 illustrate a wiping device 70' which is similar to the device 70 of FIGS. 13 and 14, also having an array of circular wiping elements 74' extending from a base 72'. However, each of the wiping elements 74' have a circular pedestal wall 76' with an angular or sloping annular side 79' instead of a curved or concave profile. Of course, as tongue cleaners, the wiping devices 70 and 70' may be mounted or formed in a toothbrush handle 12, as shown in FIGS. 13 and 15.

Note that the angular profile illustrated in the cross-sectional view of FIG. 16 could be implemented (instead of a curved or concave profile) in any of the embodiments herein, including the embodiment of FIGS. 5–10.

Figure 17:
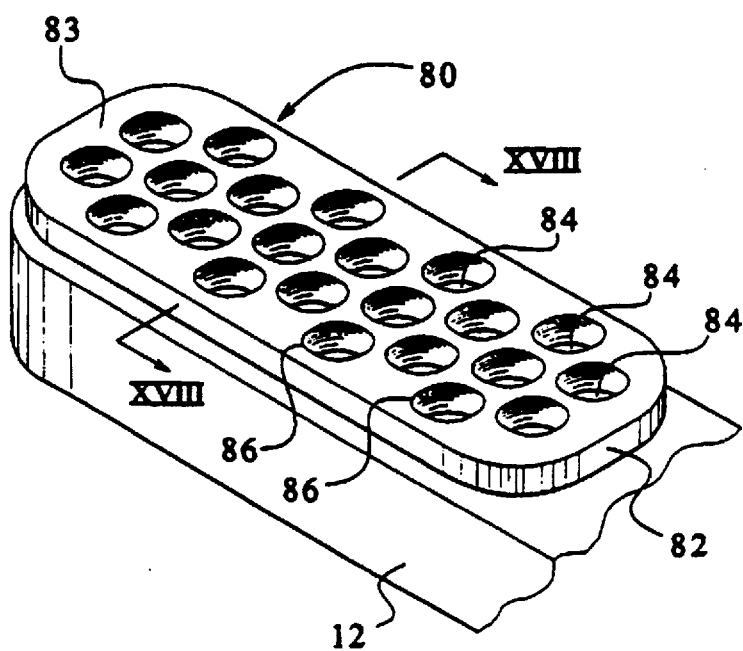
FIG. 17 is a fragmentary perspective view of a "Swiss-cheese" style wiping device having an array of shaped spheroidal apertures with annular wiping edges, the device being mounted on a toothbrush handle.

Another planar-directional embodiment is illustrated in FIGS. 17 and 18A–18D which is sort of a "reverse" of the embodiments of FIGS. 13–16. Specifically, a hole-type wiping device 80 is shown in FIG. 17, which is formed by a plate-like base 82 with an upwardly-facing planar wiping side 83. The base 82 has an array of shaped apertures 84 disposed therein, giving the wiping device 80 a sort of "Swiss-cheese" appearance at the wiping side 83. Each of these apertures 84 open at the wiping side 83 through an inwardly-directed annular wiping edge 86.

Figure 18A:
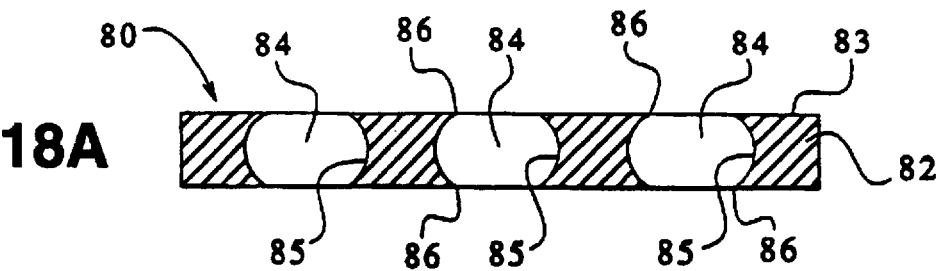
FIG. 18A is a sectional view taken generally along line XVII—XVII of FIG. 18, showing a double-sided embodiment.

As illustrated in the cross-sectional view of FIG. 18A, each aperture 84 has a recessed, curved or sloped annular wall 85. The embodiment of FIG. 18A, is double-sided, having a wiping side at the top and bottom, being operable from the top or bottom. Specifically, each the apertures 84 have a generally spheroidal shape, giving each aperture 84 an oval-shaped cross-section which is open at the wiping edge. Thus, the cross-section as viewed perpendicularly to the wiping side 83 reveals that the aperture 84 undercuts the wiping side 83 at the annular wiping edge 86. The undercut annular wiping edges 86 provide a multi-directional scoop-like cleaning effect when moved over a surface such as a tongue. Accordingly, these wiping device 80 may also be conveniently mounted into the handle of a toothbrush 12.

Figure 18B:
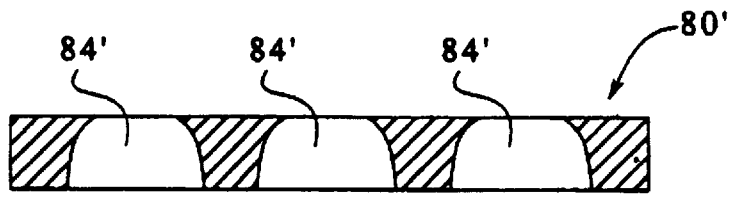
FIG. 18B is a sectional view showing an alternative single-sided open embodiment.
Figure 18C:
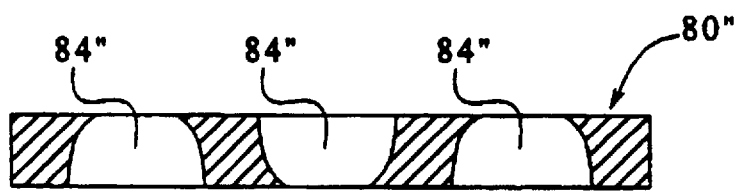
FIG. 18C is a sectional view showing an alternative up/down double-sided open embodiment.
Figure 18D:
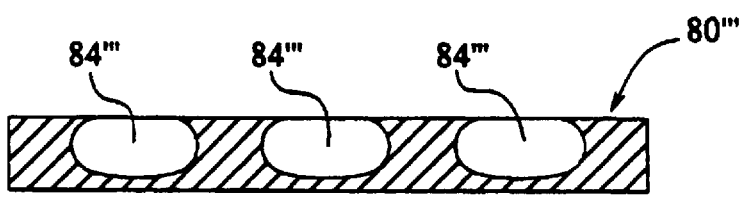
FIG. 18D is a sectional view showing an alternative single-sided partially closed embodiment.

Alternative configurations of this "Swiss cheese" embodiment are shown by example in FIGS. 18B–18C, showing various aperture shape possibilities. The embodiment shown in FIG. 18B is a single-sided wiper 80', having an open bottom and apertures 84' not having an undercutting shape. FIG. 18C shows an alternative wiper 80" with apertures 84" shaped as in FIG. 18B, but wherein the apertures 84" are alternating in up/down orientation. FIG. 18D shows a device 80''' which is also single-sided, but with apertures 84''' having closed bottoms.

Now turning to FIG. 19, the invention may also be embodied in a ring-shaped wiper device 90 shown mounted on a toothbrush handle 12. The ring-shaped wiper device 90 has two concentric annular wiping edges—an outwardly-directed annular wiping edge 92 and an inwardly-directed annular wiping edge 93. Both of these annular wiping edges 92 and 93 have an undercut shape. The inwardly-directed wiping edge 93 is formed by an aperture 94 in the device 90, similar to the aperture 84 of the embodiment of FIGS. 17 and 18A–18D.

The ring-shaped wiping device 90 may have a closed-bottom aperture 94, as illustrated in FIG. 20A, or a similar ring-shaped wiping device 90' may be provided in an embodiment having an open-bottom aperture 94', as shown in FIG. 20B.

Still another exemplary wiper device 100 is illustrated in FIGS. 21 and 22. The wiper device 100 has a plurality of topside-operable wiping elements 102 and bottom-operable wiping elements 104 which are alternatingly arranged and which are separated and defined by generally rectangular apertures or through-holes 106. As shown by FIG. 22, the wiping elements 102, 104 each have a pair of opposed wiping edges 108. The illustrated alternating embodiment is suitable for double-sided operation at either its top or bottom.

It should be understood that various changes and modifications to the presently preferred embodiments described herein will be apparent to those skilled in the art. For example, teeth wiping elements can be configured in many different shapes, so long as the teeth or wiping elements have an undercut scoop-like side toward the wiping direction. Also, as mentioned, wiping devices according to the prescribed shape may also be formed of rigid material. Such changes and modifications may be made without departing from the spirit and scope of the present invention and without diminishing its attendant advantages. It is, therefore, intended that such changes and modifications be covered by the appended claims.

What is claimed is:

1. A tongue cleaner configured for wiping a tongue along a bi-directional wiping axis, comprising:

a base; and at least one flexible wiping element including:

a pedestal wall projecting from said base, the pedestal wall having a first end connected to the base and a second free end spaced from the base, the pedestal wall having two scoop-like sides which are oppositely-facing, parallel and extending between the base and the free end, wherein the pedestal wall has a varying thickness between said scoop-like sides which increases in a direction toward the free end;

a pair of elongate wiping edges at said free end arranged in an oppositely-directed, parallel manner, said edges being adapted for engaging and abrading said surface, each of the wiping edges being formed at an undercutting termination of a respective one of the curved sides where the respective curved side meets the free end.

2. The tongue cleaner according to claim 1, wherein said scoop-like side has a curved, concave profile.

3. The tongue cleaner according to claim 1, wherein a plurality of said flexible wiping elements are provided, said wiping elements being arranged parallel to each other and transversely to said wiping axis.

4. The tongue cleaner according to claim 3, wherein facing scoop-like sides of adjacent pedestal walls are shaped as a partial cylinder.

5. The tongue cleaner according to claim 4, wherein respectively facing scoop-like sides of adjacent wiping elements are formed by a plurality of generally cylindrical bores extending through said tongue cleaner transversely to said axis.

6. The tongue cleaner according to claim 1, further comprising a toothbrush handle having a toothbrush head, the base being mounted to the toothbrush handle at an end opposite said toothbrush head.

7. The tongue cleaner according to claim 1, further comprising a plurality of said grooves in said free end which run generally along said wiping axis.

8. The tongue cleaner according to claim 1, further comprising a plurality of slots extending through the wiping element from the free end at least partially to the base, the slots being aligned generally along said wiping axis.

9. The tongue cleaner according to claim 1, further comprising a lengthwise channel disposed in said free end centrally between the wiping edges.

10. The tongue cleaner according to claim 1, wherein said wiping element is generally straight such that said elongate wiping edges are generally linear.

11. The tongue cleaner according to claim 1, wherein said wiping element is generally annular, such that said elongate wiping edges are generally circular.

12. A tongue cleaner comprising:

a wiping device configured for wiping a tongue along a bi-directional wiping axis, the wiping device including:

a base;

at least one wiping element including: a pedestal wall projecting from said base, the pedestal wall having a first end connected to the base and a second free end spaced from the base, the pedestal wall having two scoop-like sides which are oppositely-facing, parallel and extending between the base and the free end, wherein the pedestal wall has a varying thickness between said scoop-like sides which increases in a direction toward the free end; and a pair of elongate wiping edges at said free end arranged in an oppositely-directed, parallel manner, said edges being adapted for engaging and abrading said surface, each of the wiping edges being formed at an undercutting termination of a respective one of the curved sides where the respective curved side meets the free end; and a toothbrush handle having a toothbrush head, the base being mounted to the toothbrush handle opposite the toothbrush head.

13. The tongue cleaner according to claim 12, wherein said scoop-like side has a curved, concave profile.

14. The tongue cleaner according to claim 12, wherein said wiping device includes a plurality of said wiping elements arranged parallel to each other and transversely to said wiping axis.

15. The tongue cleaner according to claim 14, wherein facing scoop-like sides of adjacent pedestal walls are shaped as a partial cylinder.

16. The tongue cleaner according to claim 15, wherein respectively facing scoop-like sides of adjacent wiping elements are respectively formed by a plurality of generally cylindrical bores extending through said wiping device transversely to said axis.

17. The tongue cleaner according to claim 12, further comprising a plurality of said grooves in said free end which run generally along said wiping axis.

18. The tongue cleaner according to claim 12, further comprising a plurality of slots extending through the wiping element from the free end at least partially to the base, the slots being aligned generally along said wiping axis.

19. The tongue cleaner according to claim 12, further comprising a lengthwise channel disposed in said free end centrally between the wiping edges.

20. The tongue cleaner according to claim 12, wherein said wiping element is generally straight such that said elongate wiping edges are generally linear.

21. The tongue cleaner according to claim 12, wherein said wiping element is generally annular, such that said elongate wiping edges are generally circular.

* * * * *